US012016887B2

(12) United States Patent
Mitteness

(10) Patent No.: US 12,016,887 B2
(45) Date of Patent: Jun. 25, 2024

(54) COMPOSITIONS AND METHODS FOR REDUCING METHANE PRODUCING BACTERIA IN ANIMALS

(71) Applicant: Camas Incorporated, Le Center, MN (US)

(72) Inventor: Bradley M. Mitteness, Ghent, MN (US)

(73) Assignee: Camas Incorporated, Le Center, MN (US)

( * ) Notice: Subject to any disclaimer, the term of this patent is extended or adjusted under 35 U.S.C. 154(b) by 43 days.

(21) Appl. No.: 16/624,814

(22) PCT Filed: Jun. 19, 2018

(86) PCT No.: PCT/US2018/038317
§ 371 (c)(1),
(2) Date: Dec. 19, 2019

(87) PCT Pub. No.: WO2018/236894
PCT Pub. Date: Dec. 27, 2018

(65) Prior Publication Data

US 2020/0121730 A1 Apr. 23, 2020

Related U.S. Application Data

(60) Provisional application No. 62/522,315, filed on Jun. 20, 2017.

(51) Int. Cl.

| | |
|---|---|
| ***A61K 35/57*** | (2015.01) |
| ***A23K 10/20*** | (2016.01) |
| ***A23K 50/10*** | (2016.01) |
| ***A61K 9/00*** | (2006.01) |
| ***C07K 16/02*** | (2006.01) |
| ***C07K 16/12*** | (2006.01) |

(52) U.S. Cl.
CPC .............. *A61K 35/57* (2013.01); *A23K 10/20* (2016.05); *A23K 50/10* (2016.05); *A61K 9/0056* (2013.01); *C07K 16/02* (2013.01); *C07K 16/12* (2013.01); *Y02P 60/22* (2015.11)

(58) Field of Classification Search
CPC ........ A61K 35/57; A23K 10/20; A23K 50/10; C07K 16/02; C07K 16/12; Y02P 60/22
See application file for complete search history.

(56) References Cited

U.S. PATENT DOCUMENTS

| | | | | |
|---|---|---|---|---|
| 6,036,950 A | 3/2000 | Baker | | |
| 7,820,171 B2 * | 10/2010 | Maiti | A61P 1/00 424/130.1 | |
| 7,883,701 B2 | 2/2011 | Cook et al. | | |
| 2005/0175602 A1 * | 8/2005 | Cook | C07K 16/02 424/130.1 | |
| 2008/0254129 A1 * | 10/2008 | Maiti | A61P 1/00 424/130.1 | |

FOREIGN PATENT DOCUMENTS

CA 2629790 A1 10/2008

OTHER PUBLICATIONS

Cook et al. "Orally administered anti-*Escherichia coli* O157:H7 chicken egg yolk antibodies reduce fecal shedding of the pathogen by ruminants", Canadian Journal of Animal Science, 85(3), 2005, pp. 291-299. (Year: 2005).*
Cook et al., "Avian (IgY) anti-methanogen antibodies for reducing ruminal methane production: In vitro assessment of their effects", Australian Journal of Experimental Agriculture, 2008, 48(2), pp. 260-264. (Year: 2008).*
Mirzaei-Aghsaghali, A. and Maheri-Sis, N. "Factors affecting mitigation of methane emission from ruminants: Microbiology and biotechnology strategies" (2016) J Anim Behav Biometeorol v.4, n. 1, p. 22-31.
International Search Report and Written Opinion issued for PCT/US2018/038317, dated Sep. 27, 2018.
Henderson, G., et al. "Rumen microbial community composition varies with diet and host, but a core microbiome is found across a wide geographical range" (2015) Scientific Reports vol. 5, Article No. 14567.
Subharat, S., et al. "Vaccination of cattle with a methanogen protein produces specific antibodies in the saliva which are stable in the rumen" (2015) Veterinary Immunology and Immunopathology, vol. 164, Issues 3-4, pp. 201-207.
Search Report issued for European patent application No. 18820125.5, dated Feb. 19, 2021.

* cited by examiner

*Primary Examiner* — Timothy P Thomas
(74) *Attorney, Agent, or Firm* — Westman, Champlin & Koehler, P.A.; Z. Peter Sawicki; Amanda M. Prose

(57) ABSTRACT

Compositions for reducing the emission of methane by ruminant animals are disclosed. The compositions include avian antibodies against methanogens generally found in the rumen of the animals. Egg contents of eggs from female birds inoculated with immunogenic compositions containing one or more methanogens or antigens derived from methanogens are used. The antibodies in the egg contents may be used directly without further purification, may be partially purified or purified. The compositions may be administered in drinking water or in animal feed. Administering of the anti-methanogenic composition reduces the emission of methane and increases the efficiency of feed conversion.

11 Claims, No Drawings

COMPOSITIONS AND METHODS FOR REDUCING METHANE PRODUCING BACTERIA IN ANIMALS

CROSS-REFERENCE TO RELATED APPLICATION

This Application is a Section 371 National Stage Application of International Application No. PCT/US2018/038317, filed Jun. 19, 2018 and published as WO 2018/236894 on Dec. 27, 2018, in English, which claims priority to U.S. provisional patent application Ser. No. 62/522,315, filed Jun. 20, 2017, the contents of which are hereby incorporated by reference in their entirety.

FIELD

The disclosure relates to compositions and methods for improving feed conversion in animals and reducing methane production by animals.

BACKGROUND

Livestock is alleged to be a major threat to environment, as about 18% greenhouse gas emissions have been attributed to this sector. An estimated 12-30% of total atmospheric methane is produced by ruminants Cattle and other ruminant animals produce methane in normal fermentation processes, when microorganisms in their stomach break down fibers in grasses and grains they eat. Besides having a significant impact on global warming, methane formation also results in loss of dietary energy to the ruminant.

The microbial populations in the rumen include the group Archaea. Archaea includes a distinct group of microbes, called methanogens that produce methane in ruminant fermentation. Methanogens colonize protozoa in the rumen and metabolize hydrogen formed by some fermentative microbes to form methane.

Strategies including chemical suppression and biotechnological interventions have been investigated to attenuate methane production and improve feed efficiency. However, there is growing concern over the use of chemical inhibitors in animals used for human consumptions, and possibility in developing chemical resistant methanogens.

SUMMARY

In one aspect, the present description relates to a method of reducing methane gas production from an animal including administering an anti-methanogen composition. The anti-methanogen composition includes egg contents from an egg laid by a hen, wherein the egg contents include avian antibodies and the egg contents are produced from eggs laid by female birds inoculated with an immunogenic composition including methanogens or antigens derived from methanogens and wherein administration of the composition binds and/or inactivates the methanogens in the rumen of the animal and reduces the production of methane in the animal.

In another aspect, the present description relates to a method of enhancing feed conversion in an animal including administering an anti-methanogen composition. The anti-methanogen composition includes egg contents from an egg laid by a hen, wherein the egg contents include avian antibodies and the egg contents are produced from eggs laid by female birds inoculated with an immunogenic composition including methanogens or antigens derived from methanogens and wherein administration of the composition binds and/or inactivates the methanogens in the rumen of the animal and increases the production of volatile fatty acids in the animal.

In a further aspect, the present description relates to a composition for reducing the methane production in an animal. The anti-methanogen composition includes egg contents from an egg laid by a hen, wherein the egg contents include avian antibodies and the egg contents are produced from eggs laid by female birds inoculated with an immunogenic composition including methanogens or antigens derived from methanogens and wherein administration of the composition binds and/or inactivates the methanogens in the rumen of the animal and increases the production of volatile fatty acids in the animal.

DETAILED DESCRIPTION OF ILLUSTRATIVE EMBODIMENTS

The present disclosure includes methods and compositions administered to an animal to reduce the production of methane from animals and enhance the conversion of animal feed. Anti-methanogenic (AM) compositions can be administered to the animal and can include avian antibodies from eggs of female birds inoculated with one or more methanogens or antigens derived from methanogens. Treating the animal with the AM compositions described herein can improve feed conversion and reduce the formation and/or emission of methane from methanogens in the rumen of animals.

Without being bound by any theory, the reduction in methane emission can be due to binding and/or inactivation of the methanogens in the rumen of the animal. The binding and/or inactivation of the methanogens may reduce colonization of the protozoa in the rumen by the methanogenic bacteria. The administration of the composition to the animal can also enhance the conversion of animal feed. The enhanced conversion of animal feed may be due to, for example, enhanced production of volatile fatty acids such as propionate production leading to improved tissue growth.

"Anti-methanogenic composition" as used herein refers to compositions that include antibodies that can bind and/or inactivate methanogens. "Anti-methaonogenic composition" may also be referred to herein as "AM composition".

"Avian antibodies" as used herein refers to and include purified avian antibodies, partially purified avian antibodies or complete egg contents that include the avian antibodies.

"Egg powder" as used herein refers to spray dried egg contents and can include purified avian antibodies, partially purified avian antibodies and/or unpurified egg contents that include antibodies.

"Methanogens" as used herein refers to microbes that produce methane in the rumen of an animal. Methanogens generally scavenge for and/or metabolize hydrogen in the rumen to produce methane.

"Volatile fatty acids" as used herein refers to, for example, acetic acid (acetate), butyric acid (butyrate) and propanoic acid (propionate) and the like. Volatile fatty acids are produced in large amounts through ruminal fermentation and are an important source of energy supply to a ruminant animal.

The compositions of the present disclosure can include antibodies, for example, avian antibodies. The antibodies can bind and/or neutralize one or more methanogens in the rumen of an animal. The compositions generally include avian antibodies from eggs of female birds inoculated with one or more methanogens and/or antigens derived from methanogens. The avian antibodies can be against the one or more methanogens. The avian antibodies in the egg contents can bind and prevent the methanogens from generating methane in the rumen of an animal and improve feed conversion.

Methanogens may bind and colonize protozoa that enables the methanogens to scavenge and utilize the hydrogen generated during digestion of the feed in the rumen. The methanogens can enable the reaction between hydrogen and $CO_2$ and/or methyl groups to produce methane. In one embodiment, the avian antibodies may prevent the methanogens from colonizing the protozoa in the rumen of the animal to reduce the production and emission of methane by the animals.

The AM compositions described herein can include avian antibodies against one or more methanogens and/or antigens derived from methanogens. Methanogens can include a variety of Archaea microbes. Examples of methanogens include, for example, *Methanobrevibacter gottschalkii, Methanobrevibacter ruminantium, Methanobrevibacter stadtmaniae, Methanobrevibacter smithii, Methanobacter formicium, Methanobrevibacter arboriphilus, Methanosarcina barkeri, Methanosphaera* sp. *Methanomassiliicoccaseae*-affiliated groups and the like. Avian antibodies against other methanogens may also be used and are within the scope of the present disclosure.

The AM compositions described herein include avian antibodies. AM compositions that include non-avian antibodies are also contemplated and are within the scope of this disclosure. AM compositions can be spray-dried, powdered compositions. Alternatively, the AM compositions can be liquid compositions that include the avian antibodies. In one embodiment, the liquid AM compositions can be suspensions or solutions derived from the addition of spray-dried powder to water or other liquids. The antibodies included in the AM compositions can be purified antibodies, partially purified antibodies or unpurified antibodies, i.e. complete egg contents.

By partially purified antibodies, it is meant that the antibodies are not purified to homogeneity prior to use and that some of the components of egg contents, e.g. lecithin, may be removed from the whole egg contents prior to use. In one exemplary embodiment, egg yolks are separated from the whites and used in the anti-methanogen compositions. In another exemplary embodiment, the egg contents are water extracted prior to use in the anti-methanogen compositions.

In one embodiment, the AM compositions can include unpurified egg contents. The egg contents can be whole egg contents and includes all of the components that are present within the whole egg contents.

In one embodiment, the AM compositions can include purified antibodies from the eggs of female birds inoculated with the methanogens as described herein. The purified antibodies can include, for example, IgY. The purified antibodies can also include other avian immunoglobulin molecules, for example, IgY, IgM and IgA.

In some exemplary embodiments, the avian antibodies can be purified antibodies, partially purified egg contents and/or whole egg contents that are spray dried to a powder and stored for long term usage. Stabilizers such as trehalose may be included prior to or after spray drying. The avian antibodies can be from female birds inoculated with one specific target antigen, i.e. one methanogen that may be pooled and dried for storage. The avian antibodies can be from female birds inoculated with more than one specific target antigen, i.e. one or more methanogens that may be pooled and dried for storage. Avian antibodies may also be pooled from eggs derived from birds wherein the birds are inoculated with different antigens but the antibodies and/or egg contents are pooled when incorporated into an AM composition.

In one embodiment, the AM compositions can be formulated for administration in drinking water. The avian antibodies may be in the form of dried powder or a liquid and added to drinking water or other liquids when desired for administration to the animal. In some embodiments, the drinking water may not include any added salts that act as a buffering system. Salts may be present in the avian antibody preparation. Any salt that may be present in the avian antibody preparation is diluted when the avian antibody is added to the drinking water and may or may not be sufficient or capable of acting as a buffer. In some embodiments, the composition includes drinking water and the avian antibodies.

Providing the antibodies through drinking water can be advantageous for large-scale delivery of antibodies to a number of animals at one time. This eliminates the need to deliver the compositions individually to each animal.

In another embodiment, the AM composition can be administered in the feed as dried powder. The dried powder may be incorporated into the feed of the animals and can be ingested during the daily consumption of animal feed. In another embodiment, the animal feed may be coated with a liquid that can include the anti-methanogenic antibodies. Other methods of delivering the avian antibodies are also within the scope of this description.

Avian antibodies can be raised against any of the one or more of the methanogens by using the methanogens or methanogen components as antigens or immunogens in hens. Hens are inoculated with one or more methanogens. The eggs from the inoculated hens are then collected. Methods for inoculating hens with the desired immunogens are described, for example, in U.S. Patent Publication No. US2011/0274701 to Mitteness et al. and incorporated herein by reference.

In one embodiment, female birds are inoculated with an immunogenic composition. The immunogenic composition can include one or more methanogens or antigens derived from the one or more methanogens. The immunogenic composition may also include adjuvants. A variety of adjuvants are known in the art and all are within the scope of this description. Other components may also be included in the immunogenic composition that enhance the immunogenicity or the stability of the antigens.

Generally, the contents of the collected eggs from hens inoculated with the one or more methanogens are separated from the egg shells. In some embodiments, the antibodies are purified or partially purified from the egg contents before inclusion or use in an AM composition. In other embodiments, the egg yolks may be separated from the egg whites and incorporated into the compositions. In some embodiments, the avian antibodies are unpurified egg contents and the compositions thus include complete egg contents.

AM compositions can include antibodies against one methanogen and are referred to herein as monovalent compositions. Alternatively, avian antibodies from hens inoculated with different target antigens may be pooled prior to drying or after drying. In one embodiment, each hen is inoculated with only one target antigen. Avian antibodies derived from hens inoculated with one target antigen can be mixed with avian antibodies derived from hens inoculated with other target antigens resulting in compositions having antibodies specific for binding two or more different target antigens or methanogens. AM compositions formulated using a mixture of avian antibodies are referred to as multivalent compositions. A trivalent composition, for example, has antibodies against three different antigens.

The avian antibodies, if dried, may be used directly or as an additive to liquids. Prior to use, dried avian antibodies may be resuspended in a liquid, for example, a PBS buffer, water and the like.

The AM compositions of the present disclosure include resuspended avian antibodies. The composition can be a suspension of the avian antibodies or a solution containing dissolved avian antibodies. The composition can be used as a stock solution and further diluted into water, buffer or other liquids. The composition can, for example, can be used as stock solution and added at a desired concentration and rate to drinking water of the animals. The composition may be added to a mouthwash.

Additional components may be included in the AM compositions described herein to stabilize the composition or to enhance the activity of the composition. The components can include, for example, sugars such as trehalose that stabilize the antibodies in the composition. The components can also include preservatives. The composition may include potassium sorbate, citric acid, EDTA and the like.

In one exemplary embodiment, hens are inoculated with *M. ruminantium* and/or cellular components of *M. ruminantium*. The avian antibodies from eggs collected from these hens can be used to formulate AM compositions. The amount of the avian antibody in the composition can vary.

In one embodiment, the amount of egg powder delivered may be, for example, at least about 0.25 g of egg powder/head/day. In another embodiment, the amount of egg powder delivered may be, for example, between about 0.5 g/head/day and about 1.5 g/head/day of egg powder. In another embodiment, the amount of egg powder delivered may be, for example, at least about 0.75 g of egg powder/head/day. Amounts of egg powder outside of this range are also within the scope of this description.

The percentage of a specific avian antibody (antibody specifically against one target methanogen) in the total antibody component of the composition can vary. Spray dried egg powder can include about 4 mg of antibody per gram of egg powder. Antibody contents outside of this range are also suitable. In one embodiment, a monovalent composition has about 100 percent of the antibody present in the composition against the target antigen. In one embodiment, in multivalent compositions, the percentage of a specific antibody in the total antibody component can be at least about 10 percent of the total antibody present in the composition. For example, if egg powder is used as the source of the avian antibody and the target methanogen is *M. ruminantium*, then, in one embodiment, at least about 10 percent of the egg powder used in the composition is derived from eggs of hens inoculated with *M. ruminantium*. In a quadrivalent composition, for example, egg powders against each of four target antigens provide about 25 percent of the egg powder. Compositions with greater percentages of specific antibody against the target methanogen are suitable and all are within the scope of the description.

The compositions can be used in a variety of ruminant animals such as cattle, bovine, goats, sheep, giraffes, yaks, deer, antelope and the like. In one exemplary embodiment, the composition is used in cattle.

The present disclosure includes methods for reducing or eliminating the binding or colonization of methanogens of the protozoa in the rumen of an animal. The reduction and/or elimination of colonization by methanogens can result in decrease production of methane and concomitant decrease in the emission of methane by the animals.

The method can include applying the AM compositions described herein in the drinking water, in the feed and/or coating the feed of the animal. In exemplary embodiments, the AM composition is formulated as a concentrated composition or stock solution and delivered into drinking water through the water lines using a commercial proportioner of the animals at a desired concentration.

In one embodiment, AM compositions with avian antibodies formulated in drinking water are prepared within two days prior to administration. In another embodiment, AM compositions with avian antibodies formulated in drinking water are prepared within twenty-four hours prior to administration.

In one exemplary embodiment, the desired amount of spray dried egg powder is placed in a bucket or chemical proportioner and sufficient drinking water is added to solubilize the egg powder to create a stock solution. This stock solution is proportioned into the drinking water of the animals, for example, using a commercial proportioner at a rate calibrated for delivery of all the egg powder in a twenty-hour cycle. Thus, the desired amount of egg powder is administered to the animals throughout the twenty-four hour period whenever the animals ingest drinking water. In one embodiment, a new stock solution is made each day.

In one exemplary embodiment, the whole egg contents including the avian antibodies are converted to a powder. In another exemplary embodiment, partially purified egg contents including the avian antibodies are converted to a powder. A variety of methods are known in the art to convert whole egg contents into powders and all are within the scope of this disclosure. The amount and methods of avian antibody administered to the animal can vary and all are within the scope of this disclosure.

The animals may be treated with the AM compositions for a varying amount of time. The animals may be treated with compositions for a defined period, e.g. at least 5 days, at least 10 days, and/or at least 14 days. In one embodiment, the animals may be administered the AM composition in a continuous manner to improve feed conversion and/or decrease the daily emission of methane.

Emission of methane by an animal can be measured using a variety of ways and all are within the scope of this disclosure. In one embodiment, the methane may be measured by a sensor in the vicinity around the animals muzzle and the air from the mouth can be analyzed for the emission of methane using for example, a sulfur hexafluoride (SF6) tracer technique. This technique is described in Johnson et al. *Environ. Sci Technol.* 1994 and incorporated herein by reference.

The present description also includes methods of enhancing the conversion of feed in animals. The method can include administering an AM composition with anti-methanogen antibodies in the drinking water or in the feed of the animals. The amount of anti-methanogen antibodies can be sufficient to decrease the number of methanogens in the rumen of the animals and/or decrease the colonization of the protozoa by the methanogens in the rumen of the animals. The reduction in the number of methanogens in the rumen can enhance the production volatile fatty acids during digestion of the feed. Volatile fatty acids can include, for example, acetic acid (acetate), butyric acid (butyrate) and propanoic acid (propionate) and the like. In addition, the reduction in the number of methanogens can also enhance the propionate production and can lead to increased tissue growth. The reduction in the production of methane can lead to more availability of resources for tissue growth as opposed to waste in methane production.

The present disclosure also includes methods of operating a farm with animals. The method includes providing the AM compositions described herein to the animals. In some embodiments, the AM compositions are included in the drinking water as described herein. The compositions may be administered with the normal feeding protocols. The AM compositions may be provided continuously or intermittently. The AM compositions are provided through a commercial proportioner that continuously maintains a desired concentration of the avian antibodies in the drinking water. The animals are provided the antibodies every time they drink the water.

Methanogens can be grown in culture anaerobically in a hydrogen environment. The methanogens from culture can be isolated and used as antigens in an inoculum. In one embodiment, the methanogens may be added as a whole to the inoculum. In other embodiments, the methanogens may be inactivated prior to use in the inoculum. The inactivated methanogens culture may be further processed to isolate desired antigenic components prior to use in an inoculum.

The hens inoculated with the antigen can produce avian antibodies with binding specificity over a long period. Eggs can be collected from hens and the contents separated from the shells. The egg contents can be water extracted for egg protein according to the method of Akita et al. and incorporated herein by reference. ELISA test(s) can be performed to demonstrate the antibody binding of the homologous antibody-antigen complexes for each microorganism. By homologous it is meant that the antibodies present were from the egg contents of hens inoculated with the target antigen. They represent the satisfactory production of such antibodies within the hen(s) over a time course of several months.

In one embodiment, the test can be set up with a calculated 1 mg/ml antigen. This can then be tested against a dilution scheme of the specific or homologous antibody. The dilution of the water extracted egg protein containing the antibody can range from the greatest concentration (1:600) to the least concentration (1:38,400). Absorbance at 450 nm can be measured. Any data point over 0.5 can be considered to be significant.

Although the present description has been described with reference to some embodiments, workers skilled in the art will recognize that changes may be made in form and detail without departing from the spirit and scope of the description.

What is claimed is:

1. A method of reducing methane gas production from a ruminant comprising administering an anti-methanogen composition comprising egg contents from an egg laid by a hen, wherein the egg contents comprise avian antibodies, wherein the egg contents are produced from eggs laid by female birds inoculated with an immunogenic composition comprising *Methanobrevibacter ruminantium* (*M. ruminantium*) or antigens derived from *M. ruminantium*, wherein the egg contents are spray dried to form spray dried egg powder, wherein administration of the anti-methanogen composition binds and/or inactivates *M. ruminantium* in a rumen of the ruminant and reduces production of methane in the ruminant, wherein the method comprises administering between at least 0.25 g of the spray dried egg powder/head/day and about 1.5 g of the spray dried egg powder/head/day, and wherein the spray dried egg powder comprises 4 mg of avian antibodies per 1 g of egg powder.

2. The method of claim 1 wherein the avian antibodies in the anti-methanogen composition increase an amount of volatile fatty acids in the ruminant.

3. The method of claim 1 wherein the egg contents are whole egg contents or partially purified egg contents.

4. The method of claim 1 wherein the egg contents are administered in drinking water, by coating a ruminant feed, adding to the ruminant feed, administered orally into the mouth of the ruminant and combinations thereof.

5. The method of claim 1 wherein the immunogenic composition further comprises one or more methanogens selected from *Methanobrevibacter gottschalkii, Methanobrevibacter stadtmaniae, Methanobrevibacter smithii, Methanobacter formicium, Methanobrevibacter arboriphilus, Methanosarcina barkeri, Methanosphaera* sp. *Methanomassiliicoccaseae*-affiliated groups.

6. The method of claim 1 wherein the immunogenic composition further comprises an adjuvant.

7. The method of claim 1 wherein the avian antibodies in the anti-methanogen composition reduce colonization of protozoa in the rumen by methanogens.

8. The method of claim 1 where in the ruminant is a bovine.

9. The method of claim 1, wherein the anti-methanogen composition further comprises a stabilizer and the stabilizer is added to the egg contents prior to or after spray drying.

10. The method of claim 1, wherein the method comprises administering between at least 0.5 g of the spray dried egg powder/head/day and about 1.5 g of the spray dried egg powder/head/day.

11. The method of claim 9, wherein the stabilizer is trehalose.

* * * * *